United States Patent [19]

Olivieri

[11] Patent Number: 5,425,948
[45] Date of Patent: Jun. 20, 1995

[54] PHARMACEUTICAL COMPOSITIONS FOR THE TREATMENT AND PREVENTION OF CUTANEOUS AND ORAL MUCOUS MEMBRANE INFLAMMATIONS

[75] Inventor: Aldo Olivieri, Rome, Italy

[73] Assignee: Kemiprogress s.r.l., Rome, Italy

[21] Appl. No.: 43,493

[22] Filed: Apr. 6, 1993

[30] Foreign Application Priority Data

Apr. 10, 1992 [IT] Italy ............................. RM92A0270

[51] Int. Cl.⁶ ..................... A61K 7/16; A61K 31/74; A61K 7/26; A61K 9/14
[52] U.S. Cl. ................................. 424/401; 424/49; 424/50; 424/434; 424/435; 424/195.1; 424/489; 514/887
[58] Field of Search ............ 424/401, 434, 435, 78.03, 424/78.05, 489; 514/887

[56] References Cited

U.S. PATENT DOCUMENTS 5,175,000 12/1992 Godowski et al. ................. 424/426
5,229,378 7/1993 Ogata et al. ............................ 514/99

FOREIGN PATENT DOCUMENTS 0285367 10/1988 European Pat. Off. .
0396232 11/1990 European Pat. Off. .
2122893 1/1984 United Kingdom .
91/00728 1/1991 WIPO .

*Primary Examiner*—Thurman K. Page
*Assistant Examiner*—C. Azpuru
*Attorney, Agent, or Firm*—Darby & Darby

[57] ABSTRACT

The invention relates to pharmaceutical compositions for the treatment and prevention of cutaneous and oral mucous membrane inflammations comprising 18β-glycyrrhetic acid, benezophenanthridine alkaloids and optionally a suitable metallic salt.

4 Claims, No Drawings

PHARMACEUTICAL COMPOSITIONS FOR THE TREATMENT AND PREVENTION OF CUTANEOUS AND ORAL MUCOUS MEMBRANE INFLAMMATIONS

DESCRIPTION

The invention relates to anti-inflammation and anti-microbial compositions which can be used in dental and dermatological preparations for both medicinal and cosmetic purposes. More in particular, the invention relates to pharmaceutical compositions for the treatment of prevention of cutaneous and oral mucous membrane inflammations comprising 18$\beta$-glycyrrhetic acid, benzophenanthridine alkaloids and optionally a suitable metallic salt.

The prior art teaches 18$\beta$-glycyrrhetic acid or 3$\beta$-hydroxy-11-oxoolean-12-en-30-oic acid (hereafter referred to as glycyrrhetic acid) and a triterpenic acid obtained by hydrolysis of glycyrrhizic acid, the principal component of liquorice (Glycyrrizia glabra L.). The problems relative to its structure and configuration have been clarified by Ruzicka et. al. (Helv. Chim Acta 26, 2143, 2278 (1943)) and by Beaton, Spring (J.Chem. Soc. 1955, 3126). The acid has assumed a special practical importance thanks to its anti-inflammation, cicatrizant (acceleration of the healing process) and anti-ulcer properties, which have been experimentally demonstrated in some flogosis, wounds and ulcers. Recently a new system has been refined, for prevalently dermatological use, to formulate the glycyrrhetic acid in a phytocomplex. The said phytocomplex, known as Fitosoma (Registered Trademark, Indena, Milan) is the combination of the glycyrrhetic acid with vegetal phospholipids. The phytocomplex which results from this combination is a chemically new substance and not a simple mixture between an active ingredient and a vegetal phospholipid: its potency is considerably higher with respect to non-complexed glycyrrhetic acid. It has been observed that in this way the glycyrrhetic acid is better absorbed by the mucous membrane and skin and has a more prolonged action over a period of time. The phospholipids act as carriers, increasing the bioavailability and the speed of glycyrrhetic acid transepidermic penetration.

The prior art also teaches that benzophenanthridine alkaloids are present principally in a perennial herb originating in South America, called Sanguinaria Canadensis Linne, and the principal components are sanguinarine and chelerythrine. An extract of Sanguinaria canadensis had previously been used as the base of toothpastes, in gingivitis and periodontal complaints (see U.S. Pat. No. -A-4,145,412). At present the semi-purified forms of the alkaloids can be found in commerce and are generally sanguinarine nitrate and sulphate.

In FR-A-2152972 and 70-22029 the use of sanguinarine with thyophosphoric acid is described, to treat differing animal and human neoplasms.

It has been subsequently discovered that sanguinarine alkaloid in solution exhibits antifungal and antiprotozoid characteristics. Sanguarine is applied locally in the form of emulsion for prevention and treatment of fungal infections. It has been proven that sanguinarine antibacterial activity varies according to the connected radices, and it has also been observed that various sanguinarine salts (hydrochloride, sulphate) exhibit a certain activity with regard to some bacteria in various concentrations (M. Shamma, the Isoquiniline Alkaloids, Academic Press, New York, 1972, pg. 315–343).

IT-A-818449A/81 describes anti-microbial composition preparations comprising benzophenanthridine alkaloid salts with a mineral acid and a metallic salt, and their use in the treatment of ringworm, dyssentry, periodontitis, tooth decay, skin rumours, squamous cell carcinoma, gingivitis, in which the metallic salt can be a fluoride, a chloride, a bromide, and iodide, a sulphate, nitrate and acetate of a heavy metal, in particular stannous fluoride and sodium fluoride, present in quantities comprised between 0.1 and 3%.

All of the preceding known compositions based on benzophenanthridine alkaloids or glycyrrhetic acid are not, however, entirely satisfactory with regard to many infections of the skin and the oral mucous membrane.

It was therefore an aim to find a new composition which was much more active than those in the prior art, and which could be applied locally in such a way as not only to act as a treatment but also as a prophylaxis with regard to the most common forms of cutaneous and oral mucous membrane inflammations. The stated aim can be attained through the present invention by means of a pharmaceutical composition comprising:

a. glycyrrhetic acid, both pure and in a phytocomplex;
b. benzophenanthridine alkaloids, both pure and in the form of extract of sanguinarine; and optionally
c. a metallic salt.

The new compositions which are the object of the present invention can be used in the form of collutories (mouth washes), toothpastes, gum pastes, dental cements or in the form of creams and unguents, lotions, powders, soaps, shampoos and medicated plasters. It was surprising and unexpected to find also that the known anti-inflammatory, cicatrizant (acceleration of the healing process) and anti-ulcer actions of glycyrrhetic acid and the anti-microbial and anti-plaque actions of the benzophenanthridine alkaloids, integrated with and added to each other, are enormously increased and a final result is obtained that is clearly superior to that obtained through the use of only one of the two substances.

The object of the present invention is thus that of providing a new pharmaceutical composition for the treatment and the prevention of cutaneous and oral mucous membrane inflammations, comprising:

a. from 0.05 to 5% by weight of glycyrrhetic acid, both pure and in a phytocomplex form,
b. from 0.03 to 5% by weight of extract of sanguinaria containing from 0.4 to 50% by weight of the sanguinarine alkaloid, and optionally
c. from 0.03 to 5% by weight of a metallic salt.

The optional component c) of the new composition is chosen from the salts which are generally known from their use in similar preparations, and is preferably zinc chloride, zinc citrate, sodium fluoride, sodium monophosphate and stannous fluoride. These salts can be used alone or in a mixture.

The preparations of the new composition is usually done by dissolving: Cremophor (Polyoxyl 40 Hydrogenated Castor Oil) and glycyrrhetic acid (pure or in a phytocomplex) in a solvent while the alkaloids are dissolved in another suitable solvent. Then the glycyrrhetic acid solvent is added, as is the metallic salt. The solvents which have proved excellent in terms of results are: demineralized water, propylene glycol, vaseline, glycerine and the alcohols containing from 1 to 6 carbon atoms, such as methanol, ethanol, propanol and butanol.

The final composition obtained is preferably to be used in the treatment or the prevention of periodontitis, oral mucous membrane inflammations, and in dental caries prevention. It can further be used in the treatment and the prevention of dermatitis, ache, hematomas and superficial wounds.

The new compositions of the invention were tried out on 48 voluntary subjects for a period of 10 days with the aim of demonstrating the effectiveness of the preparation as a toothpaste and as collutory (mouth wash). To this end the subjects used the said toothpaste containing glycyrrhetic acid, benzophenanthridine alkaloids and metallic salts, and then they used the collutory (mouth wash) having the same active ingredients. At the end of the tests the plaque index (according to Loe and Silness) and the gum index (Loe and Silness) were determined. The results showed that in both tests considerable improvements were found in comparison to known products. A reduction of 71.5% as regards the plaque index and a reduction of 82.6% as regards the gum index were recorded.

EXAMPLE

| | |
|---|---|
| glycyrrhetic acid (pure or in phytocomplex) | 0.3% |
| extract of sanguinaria canadensis | 1% |
| zinc chloride | 0.07% |
| sodium monofluorophosphate | 0.8% | plus the usual additives and adjuvants normally used for preparing toothpastes. Similarly, other compositions are prepared, for the preparation of collutory (mouth wash) or other types of toothpaste, varying the quantity of the active ingredients as follows:

| | |
|---|---|
| glycyrrhetic acid | 0.1% |
| extract of sanguinaria canadensis | 0.035% |
| sodium fluoride | 0.05% |
| or | |
| glycyrrhetic acid | 0.1% |
| extract of sanguinaria canadensis | 3% |
| zinc chloride | 0.05% |
| sodium monofluorophosphate | 1% |
| glycyrrhetic acid | 0.1% |
| extract of sanguinaria canadensis | 0.05% |
| zinc chloride | 2% |
| sodium monofluorophosphate | 0.8% |

I claim:

1. Pharmaceutical compositions for the treatment and the prevention of cutaneous and oral mucous membrane inflammations, comprising:

a. from 0.05% to 5% by weight of 18$\beta$-glycyrrhetic acid, b. from 0.03 to 5% by weight of extract of sanguinaria comprising from 0.4 to 50% by weight of the sanguinarine alkaloid, and c. from 0.03 to 5% by weight of a metallic salt.

2. Pharmaceutical compositions as in claim 1, wherein the 18$\beta$-glycyrrhetic acid is used in its pure state or in a phytocomplex.

3. Pharmaceutical compositions, as in claim 1, wherein component c) is selected from the group consisting of zinc chloride, zinc citrate, sodium fluoride, sodium monofluorophosphate and stannous fluoride.

4. Pharmaceutical compositions, as in claim 1, wherein the compositions are in the form selected from the group consisting of collutories, toothpastes, gum pastes, dental cements, creams and unguents, lotions, powders, soaps, shampoos and medicated plasters.

* * * * *